United States Patent [19]

Kaplan et al.

[11] 4,341,754

[45] Jul. 27, 1982

[54] DIAGNOSTIC REAGENT FOR HERPES SIMPLEX VIRUS ENCEPHALITIS

[75] Inventors: Albert S. Kaplan; Tamar B. Kaplan, both of Nashville, Tenn.; Anthony B. Chen, Milpitas, Calif.

[73] Assignee: Vanderbilt University, Nashville, Tenn.

[21] Appl. No.: 114,739

[22] Filed: Jan. 24, 1980

[51] Int. Cl.$^3$ .................... A61K 43/00; G01N 33/56; G01N 33/60
[52] U.S. Cl. ................................ 424/1; 23/230 B; 260/112 R; 260/112 B
[58] Field of Search ................. 424/1, 12; 260/112 B, 260/112 R; 23/230 B

[56] References Cited

U.S. PATENT DOCUMENTS 4,205,057 5/1980 Whitaker .............................. 424/12

OTHER PUBLICATIONS

Chen et al., Virology, 91, 1978, pp. 234–242.
Lombardi et al., Chem. Abstracts, vol. 86, 1977, Abstract #696967.

*Primary Examiner*—Christine M. Nucker

[57] ABSTRACT

A cerebral spinal fluid diagnostic reagent for herpes simplex virus encephalitis consists essentially of the glycoprotein derived from Type 1 herpes simplex virus (HSV-1) having an approximate molecular weight of 132,000 which is antigenically reactive with HSV-1 antiserum. The reactive protein is in radiolabeled form and comprises at least 50% of the total radiolabeled protein present in the reagent.

2 Claims, 1 Drawing Figure

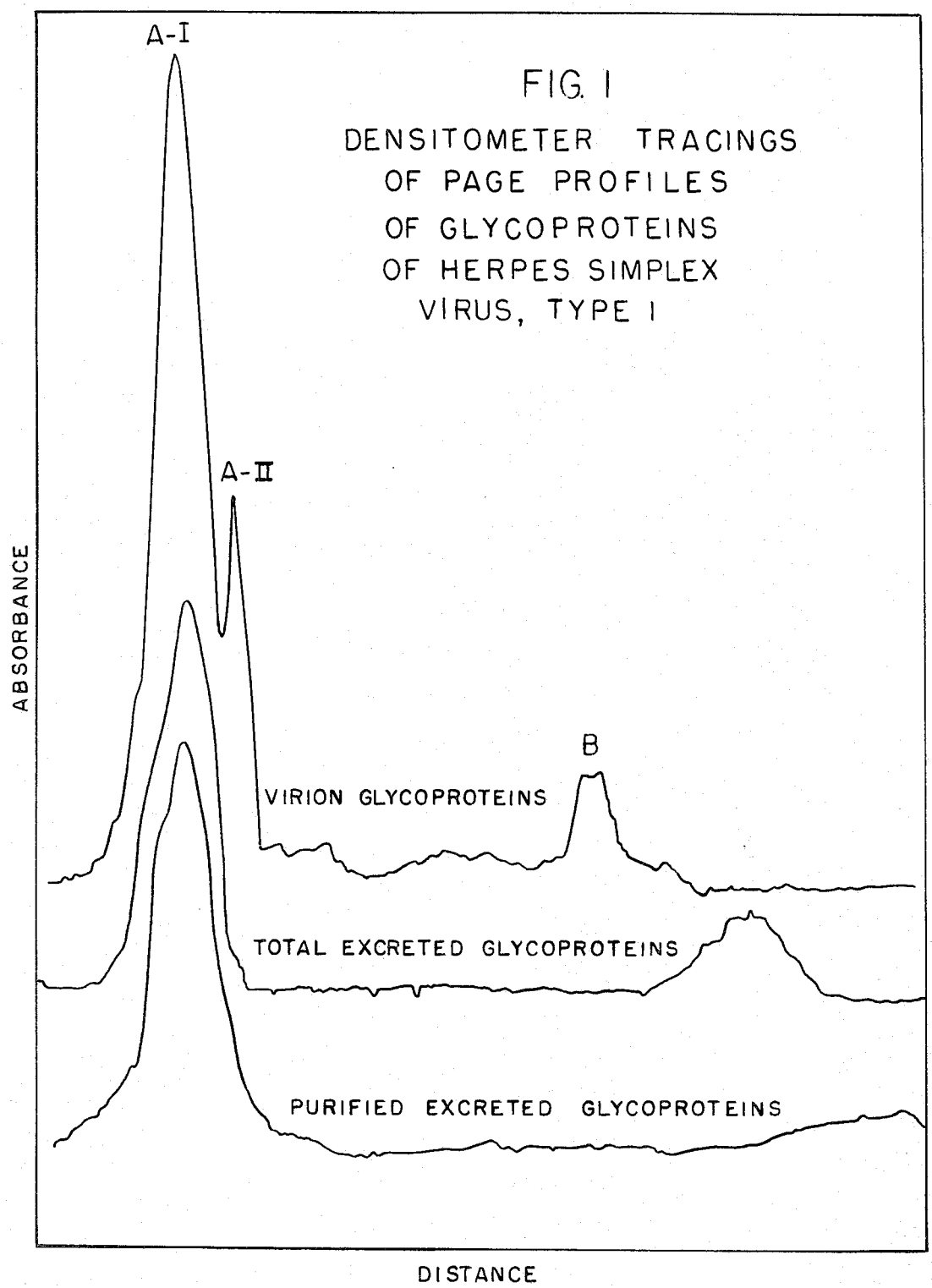

DIAGNOSTIC REAGENT FOR HERPES SIMPLEX VIRUS ENCEPHALITIS

BACKGROUND AND PRIOR ART

It was reported in 1975 that in vitro cell cultures infected with herpes simplex virus (HSV) excreted glycoproteins which were antigenically reactive with HSV antiserum. Kaplan et al, *Virology* 64, 132–143 (1975), and *Progr. Med. Virol.* 21, 1–12 (1975). The authors proposed that the released glycoproteins might represent a useful tool for detection of herpetic infections. They further stated: "The presence of such proteins detected by radioimmune assay of the cerebrospinal fluid could provide a rapid means of diagnosing herpetic encephalitis." A progress report on research work directed to the development of such an assay procedure was presented orally at the 1978 meeting of the American Society for Microbiology, Las Vegas, Nev., May 14–19, 1978. (See Abstract C61, page 287, Chen et al.) As there reported, excreted glycoproteins from HSV-infected cells were purified and radiolabeled with radioactive iodine ($^{125}$I). As further reported, the radiolabeled glycoproteins could be used to distinguish the cerebrospinal fluid (CSF) of patients with HSV encephalitis from those that did not have the disease.

The development of the specific test reagent of the present invention was described in detail by Chen et al., *Virology* 91, 234–242, published Jan. 31, 1979.

SUMMARY OF INVENTION

When cultured cells, such as rabbit kidney cells, are infected with herpes simplex virus, Type 1 (HSV-1) glycoproteins are excreted into the fluid of the cell culture medium which are antigenically reactive with HSV-1 antiserum. This can be demonstrated with respect to the residual fluid after separation of the cells and cell debris. For example, the excreted proteins may be tagged by incorporation of a radiolabeling metabolite in the medium at the time of infection of the cells, such as a radiolabeled glucosamine. However, such a solution of labeled antigenic glycoprotein could not be used as a test reagent against the CSF of patients having HSV-1 encephalitis. The degree of radioactivity is too low; in vitro radiolabeling of the protein mixture to a higher specific activity is not feasible because the antigenically reactive protein represents only a small fraction of the total protein. A further problem is that the antigenic glycoproteins become unstable with respect to their antigenicity when reacted with radioactive iodine.

The experimental work leading to the CSF diagnostic reagent of the present invention involved an identification of a specific antigenic glycoprotein, which may be obtained from cell fluid of HSV-1 infected cells, or from Type 1 herpes simplex virus. It was determined that this glycoprotein, which is highly antigenically reactive with HSV-1 antiserum, has an approximate molecular weight of 132,000. It was further determined that this glycoprotein corresponds to a protein of HSV-1, which is not exposed on the virus surface but which can be liberated by dissolving or disintegrating the virus.

It was further found that the specific antigenic glycoprotein referred to above can be used as the CSF diagnostic reagent providing it is present in the diagnostic reagent in sufficiently pure form while retaining its reactivity. The preparation of the reagent of this invention therefore requires that it be radiolabeled by a procedure which preserves at least a substantial portion of the glycolprotein in antigenically reactive form. As appreciable inactivation occurs with all methods of radiolabeling tried, a further purification after radiolabeling appears to be essential. For radioimmunoassay use, the diagnostic reagent should contain the specific reactive glycoprotein in an amount of at least 50% by weight of the total radiolabeled protein present and preferably in an amount of 65% or more of the total radiolabled protein. The test reagent thereby provides sufficient sensitivity to confirm positive and negative diagnosis of HSV-1 encephalitis using the cerebrospinal fluid test samples.

THE DRAWING

In the accompanying drawing, FIG. 1 represents plots of densitometer tracings of polyacrylamide gel electrophoresis (PAGE) profiles of glycoproteins of HSV-1, the upper curve representing the virion glycoproteins, the middle curve the total excreted glycoproteins, and the lower curve the purified excreted glycoproteins. The significance of this FIGURE will be further discussed in the following description of the invention.

DETAILED DESCRIPTION

The diagnostic reagent of the present invention for the first time makes possible the early detection of herpes simplex virus encephalitis without the need for invasive procedures, such as brain biopsy, and such early detection is essential for effective treatment. It was previously known that HSV antibody may be found in the cerebrospinal fluid (CSF) several days after the onset of the disease. See Pauli et al., *Arch. Virol.* 53, 139–155 (1977). However, no established test procedure has been provided for such antibody detection, and detectable amounts of antibody probably do not appear until the latter stages of the disease. Further, the presence of HSV antibody in CSF does not necessarily confirm HSV encephalitis, since the herpetic infection may have occurred elsewhere than in the brain. See Russell et al., *Lancet* 1, 64–65 (1976).

The sensitivity of the diagnostic reagent of the present invention is such that the presence of excreted antigenic protein in the CSF can be detected during the first one or two days after the onset of the disease. Further, the same tests can be used for positive diagnosis at a later stage. HSV antibody in the CSF can be taken into account in the reading of the test, as will subsequently be further explained and illustrated.

The diagnostic reagent of the present invention can be prepared from any virulent strain of Type 1 herpes simplex virus (HSV-1), such as ATCC No. VR-260. In the experimental work leading to this invention, the HSV-1 strain used is the one designated H4, as described in Kaplan, *Virology* 4, 435–467 (1957). However, strain H4 is merely equivalent to other readily available Type 1 HSV strains, such as the cited ATCC type strain. The HSV-1 is propagated in cell culture, such as by the use of cultures of primary rabbit kidney cells. Other primary or continuous cell cultures or cell lines can be used for the propagation.

The desired level of inoculation is not critical, but should represent the introduction of multiple virions per cell. An effective inoculation level is approximately 10 to 20 plaque forming units (PFU) per cell. The inoculation of the cell culture and the recovery of the cell fluid containing the excreted glycoproteins may be carried out as described by Kaplan et al., *Virology* 64, 132–143 (1975). For example, the cell may be cultured in Eagle's medium and incubated with the virus for 20 hours at 37° C. The cell fluid is collected by low gravity centrifugation to remove the cellular debris. Viral particles (HSV) are removed from the fluid by pelleting at high gravity centrifugation (100,000 g, 1 hr.). The supernatant separated from the pelleted virus contains a solution of glycoproteins and other proteins. The specific antigenic glycoprotein used in the diagnostic reagent of this invention can be recovered therefrom by suitable purification procedures.

A desirable initial purification can be obtained by applying the solution of proteins to an adsorption column containing Con A-Sepharose as the adsorbent. This adsorbent, which is manufactured by Pharmacia Fine Chemicals, contains Concanavalan A which is a selective adsorbent for glycoprotein. The adsorbed glycoproteins can be eluted with an aqueous solution of alpha-methyl mannoside. A preferred eluting agent comprises water containing 0.05 molar (M) of the methyl mannoside containing 1 M NaCl. With this procedure, all glycoproteins are concentrated, including the desired specific antigenic glycoprotein. Considerable additional purification is required.

As the next purification stage, the eluate from the Con A-Sepharose column may be applied to a DEAE-cellulose column. The adsorbed glycoprotein may be eluted with Tris-buffer containing added sodium chloride. A preferred concentration is 0.3 M NaCl. The eluate thus obtained will contain approximately three times the concentration of the desired antigenic glycoprotein as the starting culture fluid. Other non-viral proteins will also have been eliminated. However, this concentration is still insufficient for use in the diagnostic reagent of this invention. To provide the required sensitivity for the CSF test, the specific antigenically reactive glycoprotein should be present in a concentration of at least 50% by weight, and preferably 65% by weight or more of the total glycoprotein present. To obtain the necessary purity for diagnostic reagent use, it appears that further purification by immune affinity adsorption and elution is necessary. For example, rabbit Ig can be prepared and recovered by precipitation as described by Kaplan et al., *Virology* 64, 132–143 (1975). The prepared rabbit Ig is then coupled to CNBr-activated Sepharose granules as supplied by Pharmacia Fine Chemicals. Either batch or column adsorption may be used. In a simple batch procedure, the solution containing the HSV-specific protein obtained as the eluate from the DEAE-cullulose column is applied to the immune affinity adsorbent, which has been prepared as described. For example, approximately 2 ml of the adsorbent may be used per 6 to 8 ml of the glycoprotein solution. The initial adsorption may occur with agitation at room temperature, such as for two hours, and then the mixture allowed to stand for sixteen hours at 4° C. The supernatant is removed by low gravity centrifugation, and the adsorbent washed with Triton-buffer. The desired glycoprotein is eluted with a suitable buffer at an acid pH. Since loss of antigenic activity may occur in this step during the elution under acid conditions, this should be carried out carefully. A preferred procedure is to use glycine buffer at pH 2.65, the elution being performed in about five minutes at 0° C. Immediately after elution, the eluate is neutralized, for example, with 1.5 M Tris-HCl, pH 8.8. The resulting solution should contain the desired antigenic glycoprotein in a concentration of about 69 to 71% by weight based on the total glycoprotein present.

The concentrated specific antigenic protein thus obtained is then reacted with radioactive iodine ($^{125}I$) to prepare the reagent. The iodination should be carried out with as little inactivation of the antigenic determinants. However, some loss of antigenicity must apparently be accepted, and further purification after iodination is therefore required. Based on present knowledge, the best known iodination procedure is one using chloramine-T, as described by Hunter et al. *Nature* 194, 495–496 (1962). With this procedure, preparations of the glycoprotein with specific activities of $10^7$ to $10^8$ cpm/μg of protein can be obtained. Typically, however, the concentration of the reactive glycoprotein may be reduced to about 20% by weight of the total radiolabeled protein present. Therefore, the $^{125}I$-labeled glycoprotein mixture of antigenically active and inactive components must be fractionated to complete the preparation of the reagent. This can be readily done by reapplication of the solution of the iodine-labeled glycoproteins to the immune affinity adsorbent, using the same procedure as described above for the adsorption and elution. If necessary, the adsorption and elution can be repeated. However, a single reapplication to the immuno-adsorbent can be expected to increase the concentration of the antigenic glycoprotein to approximately 70% by weight or more. As previously indicated, the desirable concentration of the $^{125}I$-labled antigenic glycoprotein for use as a test reagent is at least 50% by weight of the radiolabeled protein present, and preferably at least 65% by weight such as a concentration of about 70%.

After completion of the preparation of the test reagent by the procedure just described, the reagent can be stored in the frozen state. For example, by freezing the reagent solution at a temperature of −70° C. and storage at that temperature, a reasonable shelf life of the reagent can be obtained, such as one to two months. It will be understood that the reagent solution would be thawed prior to use as a test reagent.

With reference to the purification and iodination procedure just described, the following table (Table A) sets out the results of a specific experimental preparation of a test reagent. As will be noted, the final iodinated product after the immune affinity readsorption and elution had a concentration of approximately 70% by weight of HSV-specific glycoprotein based on the total protein present. The radioactivity figures appearing in the center column of the table were obtained for monitoring purposes, the cell culture having been supplied with radiolabeled glucosamine to tag the cell-excreted protein. The reagent used was [$^3H$] glucosamine (10 Ci/ml). It will be understood, however, that once the purification procedure is established that it will not be necessary to employ metaboloid labeling of the excreted protein, although there would be no objection to doing so with respect to the use of the purified product as a test reagent.

TABLE A

| Purification or Treatment Step | Purification and $^{125}$I-Labeling of Principal HSV-1 Excreted Protein | | | % Total Protein HSV-Specific |
|---|---|---|---|---|
| | Volume (ml) | Total Radioactivity (cpm × 10$^{-2}$) | (%) | |
| (a) Crude culture fluid | 300 | 4326[1] | (100) | 12 |
| (b) ConA-Sepharose 0.05 M αMM[2] | 34 | 1285 | (29.7) | 25 |
| (c) DEAE Cellulose 0.3 M NaCl | 8 | 734 | (17.2) | 33 |
| (d) Immune Affinity | 2 | 87 | (2.0) | 70 |
| (e) $^{125}$I-Iodination of (d) | | | | 20[3] |
| (f) Immune Affinity | | | | 70 |

[1] In vivo $^3$H-glucosamine-labeled glycoproteins
[2] Alpha-methyl mannoside
[3] In vitro radioiodinated protein

IDENTIFICATION OF THE SPECIFIC GLYCOPROTEIN

Electrophoresis of labeled virus-specific proteins was carried out according to the method of Laemmli, Nature 227, 680–685 (1970). Slab gels consisted of 2-cm, 5% stacking gels and 15-cm, 10% resolving gels. The resolving gel consisted of an 8.5% acrylamide gel cross-linked with N,N'-diallyltartardiamide. Protein samples were prepared for electrophoresis by dialyzing against 0.05 M Tris-HCl, pH 6.8, containing 1% SDS. The samples were then boiled at 100° for 2 min in the presence of 0.025 M dithioerythritol (DTE). After electrophoresis, the slab gels were dried and the gels were impregnated with 2,5-diphenyloxazole (PPO). PAGE profiles were obtained by fluorography using Kodak XR-5 film (Bonner and Laskey, Eur. J. Biochem. 46, 83–88 (1974).

Densitometer tracings of PAGE profiles of HSV-1 (H$_4$) glycoproteins were prepared as follows: [$^3$H]Glucosamine-labeled virions and [$^3$H]glucosamine-labeled, excreted glycoproteins were obtained from HSV-1 (H$_4$)-infected RK monolayer cell cultures prepared as described above. The virions were disrupted by sonication and prepared for electrophoresis. [$^3$H]Glucosamine-labeled glycoproteins and $^{125}$I-labeled-purified, excreted glycoproteins were electrophoresed as described above, and subjected to fluorography. The data is plotted in FIG. 1 with the "Absorbance" and "Distance" being shown in arbitrary units. The uppermost curve, representing the $^3$H-labeled virion glycoproteins, shows three main peaks, A-I, A-II, and B. These peaks correspond with glycoproteins of molecular weights of 132,000, 120,000, and 60,000, respectively. As will be noted, the $^3$H-labeled total excreted glycoproteins and the $^{125}$I-labeled purified excreted glycoproteins, as represented by the middle and lower curves, also show the peak A-I, which evidences the presence of the glycoprotein having a molecular weight of approximately 132,000. Glycoprotein A-I was further characterized by a study of the antigenic relationship between excreted HSV-1 antigen and structural viral antigens.

Rabbit serum against excreted protein (1:250) was preincubated with different dilutions of HSV virions (blocking antigen). $^{125}$I-excreted antigen (10,000 cpm) was then added. The antigen-antibody complexes were precipitated with goat anti-rabit-globulin and the number of counts precipitated was determined. In the absence of blocking antigen, 40% (4,000 cpm) of the $^{125}$I antigen was precipitated. The data is summarized below in Table B. As will be noted, the purified intact virions (HSV-1) were not very effective in blocking the reaction of $^{125}$I-excreted antigen with the antiserum. While some blocking was detectable with intact virions (33% at a dilution of virion of 1:100), the effect was considerably increased when the virions were disrupted by treatment with a non-ionic detergent (Triton X-100). This data strongly supports the conclusion that the excreted glycoprotein corresponds in antigenicity as well as in molecular size (FIG. 1) to an internal glycoprotein of HSV-1. The low level of blocking obtained with the preparation of intact virions was probably due to the presence of some broken particles in the preparation.

TABLE B

| | Antigenic Relationship Between Excreted HSV-1 Antigen and Structural Viral Antigens | |
|---|---|---|
| Blocking Antigen | Dilution | |
| | 1:100 | 1:500 |
| HSV-1 | 2670[a] (67)[b] | 3750(93) |
| HSV-1 + Triton X-100 | 67 (2) | 1850(46) |

[a] cpm precipitated
[b] $^{125}$I-precipitated, % of control

DIAGNOSTIC TESTS

The diagnostic reagent prepared as described above with reference to the procedure summarized in Table A, was subjected to a series of tests to determine whether it was capable of positively diagnosing HSV encephalitis. Cerebrospinal fluid (CSF) specimens were obtained from ten patients, six of which had HSV encephalitis as confirmed by brain biopsy, and four of which were found to be free of HSV encephalitis by brain biopsy. The procedure used was as follows:

Human cerebrospinal fluids (0.1 ml) were incubated with the required dilution of antiserum (0.02 ml) for 1 hour at 37° C. and then 16 hours at 4°. A predetermined amount of $^{125}$I-labeled HSV-1 excreted glycoprotein (0.01 ml) was added to the mixture and incubation was continued for two hours at 37° C. Goat antiserum (0.1 ml) specific for rabbit immunoglobulin was added and the mixture incubated for 2 hours at 4°. The precipitates which formed were collected by centrifugation at 3,000 g, washed twice with KI buffer, solubilized with 0.2 ml NaOH (0.1 N) and the amount of radioactivity in the precipitate was measured in a Packard scintillation spectrometer.

The data obtained are summarized below in Table C. The results show that all six CSF which were obtained from patients who had been diagnosed as HSV-encephalitis-positive by biopsy blocked the interaction of iodinated antigen with the antiserum. None of the CSF from HSV-negative controls did so. These findings have been confirmed by additional larger scale tests.

TABLE C
Radioimmune Blocking Test Using Cerebrospinal Fluids from Ten Patients

| Patient Sample No. | HSVE[1] Diagnosed by Brain Biopsy | $^{125}$I Precipitated (% of control) |
| --- | --- | --- |
| 1 | confirmed | 84.5 |
| 2 | " | 72.5 |
| 3 | " | 33.6 |
| 4 | " | 71.0 |
| 5 | " | 74.2 |
| 6 | " | 62.3 |
| 7 | not present | 115.0 |
| 8 | " | 102.5 |
| 9 | " | 111.6 |
| 10 | " | 113.0 |

[1] Herpes simplex virus encephalitis

CLINICAL DIAGNOSTIC PROCEDURE

Diagnostic test reagents prepared in accordance with the present application can be used for the detection of HSV-1 antigen or antiserum in cerebrospinal fluids. Reliable test results can be obtained either in the early or later stages of the infection. One desirable procedure is as follows:

The diagnostic test reagent (DTR) containing the A-1 glycoprotein as the principal antigen and radioiodinated (2000 cpm) is first precipitated with various dilutions of rabbit antibody to determine which will precipitate 50% of the maximal precipitable counts in the DTR (which should exceed 70% of the total counts in the DTR sample). An aliquot of the dilution of the rabbit serum is then incubated with the CSF; the DTR (2,000 cpm) is then added and the samples further incubated to allow the antibodies and antigens to react with each other.

If the CSF contains an excess of free antigens over antibodies to the HSV specific proteins, the excess antigen will be able to react with the rabbit antibodies during the first incubation period which then will not be available to the DTR (because the antibodies are present in limiting amounts); labeled antigen will therefore not be precipitated. This is diagnostic of the early stages of the disease.

If the CSF contains an excess of antibodies over free antigens, the rabbit antiserum dilution will remain free to react with the labeled antigen. Furthermore, the antibodies in the CSF will also react with antigen. More than the 50% of the maximal precipitable counts of DTR will therefore be precipitated. This is diagnostic of late stages of the disease.

Precipitation of the antigen-antibody complex is accomplished by the method of Kessler, using formalin fixed staph-aureus. See Kessler, *J. Immunol.* 115, 1617–1624 (1975).

ALTERNATE PROCESS

As an alternate method to obtain the HSV-1 specific protein, one may start with virions. Primary rabbit kidney cells (or any other cell line which gives good yields of HSV) are infected with the virus. After all the cells in the cultures have degenerated as a result of virus infection, the degenerated cells are disrupted in the culture fluid by sonic oscillation, the virus is collected, and the cellular debris is removed by several cycles of alternating high (100,000 g) and low (5,000 g) gravity centrifugation. The virus is then partially purified by centrifugation in linear sucrose gradients. The partially purified virions are disrupted with nonionic detergents (such as Triton X-100 or NP40). The glycoproteins are collected by adsorption onto ConA-sepharose and may be separated by DEAE-cellulose chromatography, as described above. Further purification by immune affinity chromatography may be necessary.

Iodination in vitro with $^{125}$I and repurification of the antigenically reactive proteins are accomplished, as described above.

We claim:

1. A cerebrospinal fluid diagnostic reagent for herpes simplex virus encephalitis, consisting essentially of the glycoprotein derived from Type 1 herpes simplex virus (HSV-1) having an approximate molecular weight of 132,000 and being antigenically reactive with HSV-1 antiserum, said reactive glycoprotein being in a radiolabeled form for radioimmunoassay use and comprising at least 50% by weight of the total radiolabeled protein present in said reagent.

2. A cerebrospinal fluid diagnostic reagent for herpes simplex virus encephalitis, consisting essentially of the glycoprotein derived from Type 1 herpes simplex virus (HSV-1) having an approximate molecular weight of 132,000 and being antigenically reactive with HSV-1 antiserum, said reactive glycoprotein being in a $^{125}$I-radiolabeled form for radioimmunoassay use and comprising at least 65% by weight of the total radiolabeled protein present in said reagent.

* * * * *